(12) United States Patent
Hohla et al.

(10) Patent No.: US 6,763,262 B2
(45) Date of Patent: Jul. 13, 2004

(54) METHOD AND APPARATUS FOR DETECTING TUMOROUS TISSUE

(75) Inventors: Alexander Hohla, Munich (DE); Gunther Leipert, Gilching (DE)

(73) Assignee: TuiLaser AG, Germering (DE)

( * ) Notice: Subject to any disclaimer, the term of this patent is extended or adjusted under 35 U.S.C. 154(b) by 351 days.

(21) Appl. No.: 09/860,365

(22) Filed: May 18, 2001

(65) Prior Publication Data

US 2002/0128557 A1 Sep. 12, 2002

(30) Foreign Application Priority Data

May 19, 2000 (EP) .............................................. 00110768

(51) Int. Cl.⁷ ................................................ A61B 6/00
(52) U.S. Cl. ........................ 600/476; 600/477; 600/478; 600/407
(58) Field of Search ................................. 600/476, 477, 600/478, 473, 407–436; 356/317, 318, 446, 448

(56) References Cited

U.S. PATENT DOCUMENTS

| | | | | |
|---|---|---|---|---|
| 5,348,018 A | * | 9/1994 | Alfano et al. | 600/476 |
| 5,369,496 A | * | 11/1994 | Alfano et al. | 356/446 |
| 5,413,108 A | * | 5/1995 | Alfano | 600/478 |
| 5,467,767 A | * | 11/1995 | Alfano et al. | 600/476 |
| 5,813,988 A | * | 9/1998 | Alfano et al. | 600/476 |
| 5,931,789 A | * | 8/1999 | Alfano et al. | 600/473 |

* cited by examiner

Primary Examiner—Henry Bennett
Assistant Examiner—Fadi H. Dahbour
(74) Attorney, Agent, or Firm—Mintz, Levin, Cohn, Ferris Glovsky and Popeo, P.C.

(57) ABSTRACT

The present invention relates to an apparatus for detecting tumorous tissue comprising at least one excitation light source 12, which first excitation light source 12 emits a first excitation light 34 of a wavelength of between 300 nm and 314 nm and includes at least one optical fiber 14 for guiding the first excitation light 34 to an object field 18 of the tissue 16 to be examined, and at least one lens 24 for projecting an auto-fluorescence signal and/or a remission signal 20 of the tissue 16, generated by the first excitation light 34, to a CCD or ICCD chip of a camera 22, as well as a data processing system 28 for processing the signals transmitted by the camera 22, said lens 24 being capable of processing UV light and being designed such that at least two images 48, 50 from different spectral regions of the fluorescent object field 18 are generated and projected to the CCD or ICCD chip, of which at least one image 48, 50 represents the UV range and another, different wavelength range of the auto-fluorescence signal and/or of the remission signal 20 of said object field 18. The invention is further directed to a method for detecting tumorous tissue.

12 Claims, 3 Drawing Sheets

METHOD AND APPARATUS FOR DETECTING TUMOROUS TISSUE

BACKGROUND OF THE INVENTION

The present invention is directed to an apparatus for detecting tumorous tissue, comprising at least one source of excitation light, which first excitation light source emits a first exciting light of a wavelength of between 300 nm and 314 nm and includes at least one optical fiber for guiding said first excitation light to an object field of the tissue to be examined, and at least one lens for projecting an auto-fluorescence signal and/or a remission signal of the tissue, generated by means of said first excitation light, to a CCD or ICCD chip of a camera, as well as at least one data processing system for processing the signals transmitted by the camera. The invention further relates to a method for detecting tumorous tissue.

Early detection of tumors is the most important prerequisite for fighting them effectively. This will also decisively improve tumor patients' prospects of being cured. Prior art methods and apparatuses for detecting tumorous tissue are based on two different diagnostic approaches. One such approach is based on laser-induced fluorescence and involves administering synthetic fluorescent dyes or synthetic porphyrin mixtures as an attempt to label as well as display any tumours present. However, this method is disadvantageous in that the said synthetic substances will sensibilize the skin, thus requiring patients to be protected from intense light over a period of several weeks. Moreover, a low fluorescence quantum efficiency makes it impossible to distinguish clearly between healthy and abnormal tissue.

For this reason, it has been tried to gain information for distinguishing between healthy and tumorous tissue through the intrinsic, UV-excited auto-fluorescence of the tissue. The spectroscopic detection of tumours and neoplasia using UV light at between 300 nm and 312 nm is described in detail in U.S. Ser. No. 5,131,398 and WO 97/06724, for example. For this purpose, the tissue's intrinsic fluorescence is excited by means of UV light at the said wavelength range, spectrally split by means of a spectrometer and then displayed. In doing so, the tissue is punctually scanned by means of a suitable optical probe. As a significant feature for distinguishing between normal healthy tissue and tumorous tissue, U.S. Ser. No. 5,131,398 discloses the intensity ratio of the native fluorescence in the fluorescence peaks at 340 nm and 440 nm.

However, one shortcoming of the prior art methods and apparatuses for displaying tumorous tissue by means of the auto-fluorescence of the tissue is that they do not provide a visual impression of the entire tumorous area or of the entire tissue area being examined.

SUMMARY OF THE INVENTION

For this reason, it is the object of the present invention to provide a generic apparatus as well as a generic method which will allow visual display of the entire tissue area under examination, at the same time clearly distinguishing normal healthy tissue from tumorous tissue.

This object is accomplished by a generic apparatus having the features of claim 1 as well as by a generic method having the features of claim 6.

Advantageous embodiments are described in the subclaims.

An apparatus according to the invention for detecting tumorous tissue comprises a lens which is capable of processing UV light and is designed such that at least two images from different spectral regions of a fluorescent object field are generated and projected to a CCD or ICCD chip of a camera, with at least one of said images representing the UV range and another wavelength range, different therefrom, of the auto-fluorescence signal and/or of the remission signal of the object field. This will ensure that the entire tissue area being examined will be made visible, at the same time clearly distinguishing normal healthy tissue from tumorous tissue.

In an advantageous embodiment of the inventive device, the lens includes a ridge prism as well as at least one achromatic UV lens. Such an array will allow the illuminated object field to be precisely subdivided into plural images of different wavelength ranges of the auto-fluorescence signal and/or of the remission signal of the object field, which will then be displayed.

In yet another advantageous embodiment of the invention, the apparatus includes a second excitation light source for emitting a second excitation light at between 312 nm and 340 nm and/or 350 nm and 410 nm. Coupling in a second excitation light source emitting a second excitation light different from said first excitation light makes it possible to determine and process further image information about the object field. In certain cases, this will increase the selectivity of the apparatus for distinguishing between normal tissue and tumorous tissue.

An inventive method for detecting tumorous tissue comprises the following steps: (a) illuminating tissue with a first excitation light of a wavelength of between 300 nm and 314 nm from a first excitation light source and generating an auto-fluorescence and/or a remission of an object field of the illuminated tissue; (b) generating at least two images from different spectral regions of the fluorescent object field by means of a camera lens and projecting them to a CCD or an ICCD chip of said camera, with at least one of said images showing the UV range and another wavelength range, different therefrom, of the auto-fluorescence signal and/or of the remission signal of the object field; (c) transmitting the image/video signals generated in the camera to a data processing system; (d) subtracting background signals from the generated image/video signals; (e) inputting said UV image into a blue channel and computing said UV image therewith and inputting the other image into a green and/or red channel and computing it therewith; (f) amplifying or diminishing the individual color channels so as to obtain a standard color setting for normal, non-tumorous tissue; and (g) evaluating the color-coded images or their color-coded image/video signals for distinguishing normal, healthy tissue from tumorous tissue. This will in turn ensure that the entire tissue area being examined will be made visible, thereby clearly distinguishing normal healthy tissue from tumorous tissue.

In an advantageous embodiment of the method of the invention two images will be generated in procedural step (b), of which one image shows the UV range and the other image shows the visible wavelength range of the auto-fluorescence signal and/or the remission signal of the object field. Subsequently color coding the two images will result in a precise representation and quantification of the different kinds of tissue.

In yet another advantageous embodiment of the inventive method, procedural step (a) comprises illuminating the tissue with light from said first excitation light source and a second excitation light source for emitting second excitation light of a wavelength of between 312 nm and 340 nm and/or 350 and 410 nm. Using a second excitation light source emitting a second excitation light which is different from said first excitation light for illuminating said tissue makes it possible to determine and process further image information from the object field. In certain cases, this will increase the selectivity of the apparatus for distinguishing between normal tissue and tumorous tissue. In procedural step (b), for example, two images may be generated, of which one image shows the UV range and another image shows the infrared range of the auto-fluorescence signal and/or the remission signal of the object field. However, this will also make it possible to generate three images in procedural step (b), of which a first image shows the UV range, the second image shows the visible wavelength range, and the third image shows the infrared range of the auto-fluorescence signal and/or of the remission signal of the object field.

In accordance with another advantageous embodiment of the method of the invention, the color-coded images or color-coded image/video signals will be evaluated in procedural step (g) by comparing and displaying the generated standard color setting for normal, non-tumorous tissue with the generated color setting for tumorous tissue. This will allow the entire tissue area being examined to be made visible, at the same time clearly distinguishing normal tissue from tumorous tissue.

In yet another advantageous embodiment of the method of the invention, the evaluation of the color-coded images or color-coded image/video signals comprises the following sub-steps of procedural step (g): (g1) canceling the gamma correction by means of a correcting function and linearizing the color channels; (g2) obtaining the ratios of the intensities of the color channels and logarithmizing the result, in which step said tissue will be characterized in that positive values will denote tumorous tissue and negative values will denote normal, healthy tissue; and (g3) averaging the brightness values of the color channels and computing them together with a ratio image obtained in procedural sub-step (g2) for illustrating the distribution geometry of the different kinds of tissue. This illustration and evaluation approach allows a very precise quantification of the different kinds of tissue.

Further objects, advantages and features of the present invention will appear from the embodiments to follow, as illustrated in the drawings, of which:

DETAILED DESCRIPTION OF THE INVENTION

Figure 1:
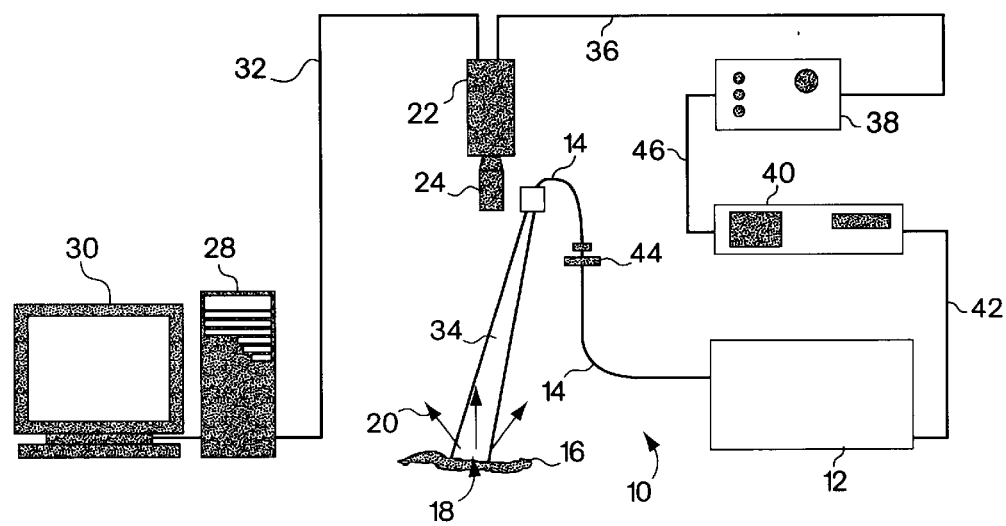
FIG. 1 is a schematic view of the apparatus according to this invention.

The schematic view of FIG. 1 shows an apparatus 10 for detecting tumorous tissue, comprising a first excitation light source 12 which emits a first excitation light 34 of a wavelength of between 300 nm and 314 nm via an optical fiber 14. Said first excitation light 34 is guided to an object field 18 of a tissue 16 to be examined. By means of a lens 24, an auto-fluorescence signal and/or a remission signal 20 generated by means of said first excitation light is projected to a CCD or ICCD chip of a camera 22. A data line 32 connects said camera 22 with a data processing system 28. Said data processing system 28 processes the signals generated by said camera 22 and displays them on a screen 30. However, other imaging or visual display devices may also be connected with said data processing system 28.

Furthermore, this view shows that said optical fiber 14 has a fiber oscillator 44 connected to it. In this embodiment, said first excitation light source 12 is a XeCl laser. However, a XeF laser or a HeCd laser may also serve as the excitation light source. Said XeCl laser is used to cause auto-fluorescence of said tissue 16. Simultaneously with the laser pulse, a sync out signal is generated which is transmitted to a pulse generator 40 via a signal line 42. Said pulse generator 40 delays said sync out signal, transmitting said delayed signal, via a data line 46, to a controller 38 of said camera 22. In this case, the delayed sync out signal is transmitted to said camera 22, via trigger signal line 36, in the form of a trigger signal. The image/video signal of said camera 22 is then forwarded, via data line 32, to a video card of said data processing system 28 for image processing.

In a further embodiment (not shown), the apparatus 10 may include a second excitation light source for emitting a second excitation light of a wavelength of between 312 nm and 340 nm and/or between 350 nm and 410 nm. A Xe, Hg or deuterium lamp or a $N_2$ laser may serve as an excitation light source for this purpose.

Figure 2:
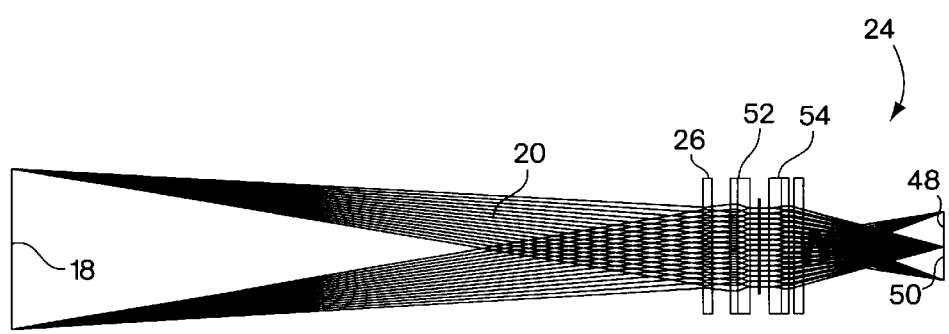
FIG. 2 is a simplified view of the beam path in a portion of the apparatus according to this invention.

FIG. 2 is a simplified view of the beam path in a portion of said apparatus 10. This view clearly shows that the lens 24 of said camera 22 includes a ridge prism 26 and a pair of achromatic UV lenses 52, 54. This will divide the auto-fluorescence and/or remission 20 of the tissue 16 from the object field 18 into two images 48, 50. Both said images 48, 50 are generated from different spectral regions of said fluorescent object field 18. Image 48 represents the UV range of the auto-fluorescence signal and/or remission signal 20 of said object field 18. Image 50 of this embodiment represents the visible range of the auto-fluorescence signal and/or remission signal 20. Said lens 24 is capable of processing UV light. However, other optically imaging elements may likewise be used for this division into two images. Also, this division may be done computationally, directly in the CCD or ICCD chip of said camera.

Figure 3:
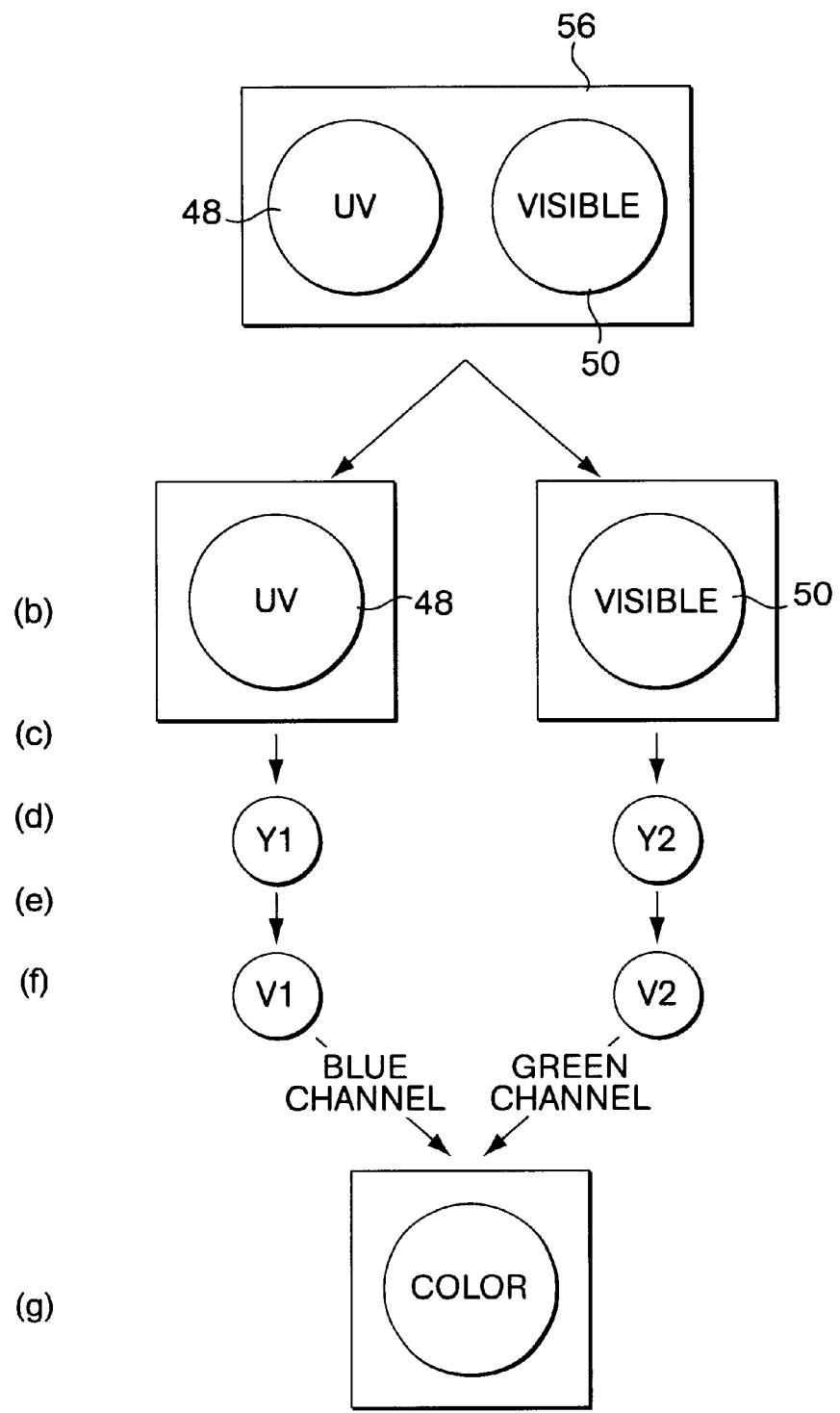
FIG. 3 is a flow chart of an embodiment of the method according to this invention.

FIG. 3 is a flow chart of an embodiment of the method according to this invention. This diagram shows that after a first procedural step (a), i.e. illuminating said tissue 16 with said first excitation light 34 and generating the auto-fluorescence and/or remission of the object field 18, two images 48, 50 are generated as a black-and-white double image 56. Image 48 shows the UV range and image 50 represents the visible wavelength range of said auto-fluorescence signal and/or said remission signal 20. These are then projected to the CCD or ICCD chip of said camera 22. The signal data are then read out from said chips and transmitted to said data processing system 28. In doing so, the background signal Y1 and Y2 are subtracted from the generated image/video signals of each individual image. The images 48, 50 are then input to into the blue or green channel and computed together therewith, and the individual color channels are amplified or diminished so as to obtain a standard color setting for normal, non-tumorous tissue. If the two color channels were of the same intensity, this would create the secondary color cyan in the computed image. However, since also normal tissue has different intensity ratios of UV as well as visible fluorescence and/or remission, the color channels need to be amplified or diminished in order to obtain the said cyan-colored image for normal tissue. Images V1 and V2 are generated. In this standard color setting, a present tumorous tissue will then appear as a bluish area since the UV share is increased or the visible share is decreased there. The color-coded images or color-coded image/video signals are therefore evaluated in procedural step (g) by comparison and display of the generated standard color setting for normal tissue with the generated color setting for tumorous tissue.

Figure 4:
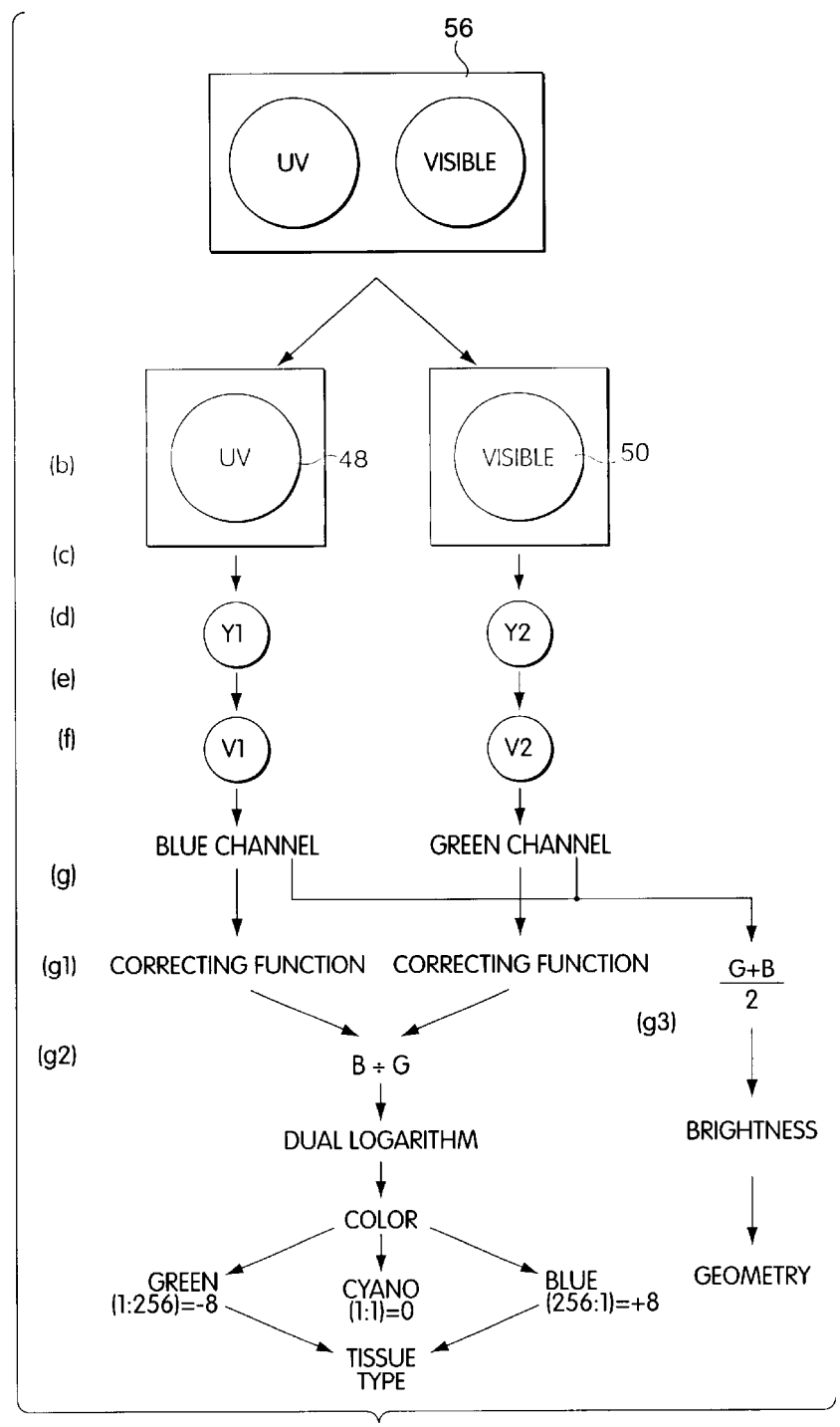
FIG. 4 is a flow chart of a further embodiment of the method according to this invention.

FIG. 4 is a flow chart of a further embodiment of the method according to this invention. In this case, the color-coded images or color-coded image/video signals are evaluated in procedural step (g) by canceling the gamma correction by a correcting function and linearizing the color channels (procedural sub-step (g1)). Moreover, in procedural sub-step (g2), the ratios of the color channel intensities are formed and the result is logarithmized, with the tissue being characterized in that positive values denote tumorous tissue and negative values denote normal, healthy tissue. At the same time, in procedural sub-step (g3), the brightness values of the color channels are averaged and computed together with a ratio image generated in procedural sub-step (g2) for displaying the distribution geometry of the different kinds of tissue.

What is claimed is:

1. An apparatus for detecting tumorous tissue, comprising:
   at least one first excitation light source for emitting a first excitation light of a wavelength of between 300 nm and 314 nm;
   at least one optical fiber for guiding said first excitation light to an object field of the tissue to be examined;
   at least one lens for projecting an auto-fluorescence signal and/or remission signal of said tissue, generated by means of said first excitation light, to a CCD or ICCD chip of a camera;
   at least one data processing system for processing signals transmitted by said camera wherein:
      said lens includes a ridge prism and is capable of processing UV light,
      said lens generates at least two images of which at least one image represents the UV range and another represents a different wavelength range of the auto-fluorescence signal and/or of the remission signal of the object field.

2. The apparatus as claimed in claim 1, wherein said lens includes at least one achromatic UV lens.

3. The apparatus as claimed in claims 1, wherein said apparatus includes a second excitation light source for emitting a second excitation light of a wavelength of between 312 nm and 340 nm and/or between 350 nm and 410 nm.

4. The apparatus as claimed in claim 1, wherein said first excitation light source is a XeF, XeCl or HeCd laser.

5. The apparatus as claimed in claims 3 or 4, wherein said second excitation light source is a Xe, Hg or deuterium lamp or a $N_2$ laser.

6. A method for detecting tumorous tissue comprising:
   a) illuminating tissue with a first excitation light of a wavelength of between 300 nm and 314 nm from a first excitation light source and generating an auto-fluorescence and/or remission of an object field of said illuminated tissue;
   b) generating at least two images from different spectral regions of said fluorescent object field by means of a lens of a camera and projecting them to a CCD or ICCD chip of said camera, of which at least one image represents the UV range and another representing a, different wavelength range of said auto-fluorescence signal and/or said remission signal of said object field;
   c) transmitting the image/video signals generated in said camera to a data processing system;
   d) subtracting background signals from said generated image/video signals;
   e) inputting said UV image into a blue channel and computing it together therewith and inputting said other image into a green and/or red channel and computing it together therewith;
   f) amplifying or diminishing the individual color channels for obtaining a standard color setting for normal, non-tumorous tissue; and
   g) evaluating the color-coded images or their color-coded image/video signals for distinguishing normal, healthy tissue from tumorous tissue.

7. The method as claimed in claim 6, wherein two images are generated in procedural step b), of which one image represents the UV range and the other image represents the visible wavelength range of the auto-fluorescence signal and/or of the remission signal of the object field.

8. The method as claimed in claim 6, wherein procedural step a), said tissue is illuminated with light from a first excitation light source as well as from a second excitation light source for emitting a second excitation light of a wavelength of between 312 nm and 340 nm and/or between 350 nm and 410 nm.

9. The method as claimed in claim 8, wherein in procedural step b) two images are generated of which a first image represents the UV range and the other image the infrared range of the auto-fluorescence signal and/or of the remission signal of the object field.

10. The method as claimed in claim 8, wherein in procedural step b) three images are generated of which a first image represents the UV range, the second image represents the visible wavelength range and the third image represents the infrared range of the auto-fluorescence signal and/or of the remission signal of said object field.

11. The method as claimed in one of claims 6 to 10, wherein the color-coded images or color-coded image/video signals are evaluated in procedural step g) by comparing and displaying the generated standard color setting for normal, non-tumorous tissue with the generated color setting for tumorous tissue.

12. The method as claimed in one of claims 6 to 10, wherein the evaluation of the color-coded images or color-coded image/video signals in procedural step g) comprises:
   g1) canceling the gamma correction by a correcting function and linearizing the color channels;
   g2) forming the intensity ratios of the color channels and logarithmizing the result, at the same time characterizing the tissue in that positive values denote tumorous tissue and negative values denote normal, healthy tissue; and
   g3) averaging the brightness values of the color channels and computing them together with a ratio image formed in procedural step g2) for illustrating the distribution geometry of the different kinds of tissue.

* * * * *